of 7,481,846 B2

United States Patent
Marsh et al.

(12) United States Patent
(10) Patent No.: US 7,481,846 B2
(45) Date of Patent: *Jan. 27, 2009

(54) METHOD OF RAPID HAIR DYEING

(75) Inventors: Jennifer Mary Marsh, Henley-on-Thames (GB); Graham Neil McKelvey, Farnborough (GB); Andrew David Wyrko, Egham (GB)

(73) Assignee: The Procter & Gamble Company, Cincinnati, OH (US)

( * ) Notice: Subject to any disclaimer, the term of this patent is extended or adjusted under 35 U.S.C. 154(b) by 345 days.

This patent is subject to a terminal disclaimer.

(21) Appl. No.: 11/233,277

(22) Filed: Sep. 22, 2005

(65) Prior Publication Data

US 2006/0064823 A1  Mar. 30, 2006

(30) Foreign Application Priority Data

Sep. 24, 2004  (EP)  ................... 04255824

(51) Int. Cl.
*A61Q 5/10* (2006.01)
(52) U.S. Cl. .................. 8/405; 8/426; 8/435; 8/619; 8/620; 8/107; 8/111; 132/202; 132/208
(58) Field of Classification Search ............ 8/405, 8/426, 435, 619, 620, 107, 111; 132/202, 132/208
See application file for complete search history.

(56) References Cited

U.S. PATENT DOCUMENTS 5,525,123 A  6/1996  Lorenz

| 6,540,791 | B1 * | 4/2003 | Dias .............................. 8/405 |
| 6,669,933 | B2 | 12/2003 | Duffer |
| 6,703,004 | B2 | 3/2004 | Narasimhan |
| 2003/0154561 | A1 | 8/2003 | Patel |
| 2004/0055095 | A1 * | 3/2004 | McKelvey et al. ............. 8/405 |
| 2004/0078906 | A1 | 4/2004 | Plos |
| 2004/0098814 | A1 | 5/2004 | Au |
| 2004/0098816 | A1 | 5/2004 | Au |

FOREIGN PATENT DOCUMENTS

| EP | 0435012 A1 | 7/1991 |
| EP | 1106166 A2 | 6/2001 |
| FR | 1592939 A | 6/1970 |
| WO | WO-01/28508 A1 | 4/2001 |
| WO | WO-01/76546 A2 | 10/2001 |
| WO | WO 200289754 A1 * | 11/2002 |
| WO | WO-2004/014328 A1 | 2/2004 |

OTHER PUBLICATIONS

PCT, Search Report, PCT/US2005/034007, Sep. 28, 2006.

* cited by examiner

*Primary Examiner*—Eisa B Elhilo
(74) *Attorney, Agent, or Firm*—Melissa Krasovec; Marianne Dressman; Tara M. Rosnell

(57) ABSTRACT

The present invention relates to a method of hair coloring and bleaching compositions providing a composition comprising i) at least one source of peroxymonocarbonate ions, ii) at least one alkalizing agent, preferably a source of ammonium ions, and iii) at least one radical scavenger, wherein said composition has a pH of up to 9.5, and applying the composition to the hair and retaining on the hair for a period of less than 20 minutes, which provide a high level of lift and lightening and the required dye deposition and grey coverage whilst reducing the concentration of peroxide, the ammonia odor and reducing the hair fiber damage.

11 Claims, No Drawings

METHOD OF RAPID HAIR DYEING

FIELD OF THE INVENTION

The present invention relates to a method of rapid bleaching and colouration of keratinous fibres.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex where they can then react with each other and suitable oxidising agents to form the end dye molecules. Due to the large size of these resultant molecules they are unable to readily diffuse out of the hair during subsequent washing with water and/or detergents; hence delivering the consumer-desired permanency of colour. The reaction typically takes place in an aggressive environment at approximately pH 10 in the presence of an alkalizing agent and in the presence of an oxidizing agent. Moreover, the consumer repeats this process regularly in order to maintain the desired hair colour shade and the intensity of colour and to ensure continual, even coverage of the hair including coverage of new hair growth.

However, despite the fact that commercial hair dyeing products have been available for many years, the products still exhibit a number of consumer-related deficiencies. In particular, the application of hair dye products is still a relatively time consuming process and it may take the consumer over an hour to mix, apply, wait for the colour to develop and remove the product; before drying and restyling. Since for most consumers the hair dyeing process is a regular part of their beauty routine it would be highly desirable if the time required to dye the hair could be reduced whilst still meeting all of the other requirements of; ease of application, low odour, and especially of course the delivery of the required hair colour, particularly for consumers requiring significant changes and/or levels of lift in the resultant colour.

A number of attempts have been described in the literature to reduce the application time required to dye hair, for example by the use of oxidative hair dye or bleach compositions comprising carbonate. For example;

WO01/28508 describes hair dyeing and bleaching compositions comprising an oxidising agent, hair colouring agents and ammonium carbonate and or carbamate which provides improved bleaching and colouring with reduced odour and hair damage without the need for buffering agents, pH modifiers or hair swelling agents. The compositions are applied to the hair for a time period of from 1 to 60 minutes.

FR1592939 describes a hair dyeing composition comprising oxidative dyes, ammonium carbonate and hydrogen peroxide at pH 7-9 which provides effective dyeing in a fairly short period of time.

EP435012 describes hair-dyeing compositions, which require a short dyeing time, create little damage to hair, and no irritating odour after dyeing comprising a carbonate source, a non odour generating alkali hydrogen peroxide and a buffer solution. Similarly, EP1106166 describes hair dye compositions comprising ammonia, carbonate (other than ammonia salt), transition metal salt and chelating agent which do not give off an irritating odour, have low skin irritation and can change the hair colour into a lighter tone in a short time.

WO04/014328 describes one step hair colouring compositions comprising peroxide oxidizing agents, specific oxidizing agents and at least one water soluble carbonate releasing salts which more effectively deliver colour wherein the composition is applied for a period of from 2 to 60 minutes.

Other attempted solutions have been described in U.S. Pat. No. 6,703,004 which describes hair bleaching compositions comprising an aqueous oxidising agent, persulphate, and a hydrophilic oil, in amounts sufficient to provide a mixture containing 3-5% active oxygen, and 0.7-1.2 meq/gm alkalinity, wherein the composition is capable of bleaching the hair in 10 to 30 minutes. Similarly, U.S. Pat. No. 6,669,933 describes an aqueous hair colouring composition for oxidatively colouring hair in less than 12 minutes comprising a dye and developer mixture, a free alkalinity concentration of 0.2-0.75 meq/gram and hydrogen peroxide.

US2004/0078906 describes a process for rapid dyeing and decolouration of keratin wherein a specific direct dye is applied to the fibres for a leave in time of less than 5 minutes.

Alternative attempts to reduce the application time of hair dyes on head involve methods which require short consecutive treatments of hair colourants whereby the colour change is achieved gradually after time. For example WO01/76546 describes a method of colouring hair comprising the steps of applying a hair colour altering composition to hair and leaving it on hair for about 0.5 to 15 minutes, wherein this method is repeated from once a month to about 3 times a day.

US2003/0154561 describes a method of applying an oxidative shampoo for a time period of from 5 seconds to 5 minutes whereby the treatment is repeated between 2 to 30 times and the time interval between treatments is 8 hrs to 30 days. Similarly, US2004/0098814 describes a method of permanently whereby the hair is subjected to a number of consecutive short treatments whereby the treatment comprises a dye intermediate in a shampoo or conditioner base, a water soluble carbonate releasing salt and a water soluble ammonium salt. US2004/0098816 also describes a method for the gradual permanent colouring of hair which includes subjecting the hair to a number of treatments having a set time interval between them, wherein the treatment compositions comprise ammonium carbonate in combination with a chelant.

However, none of these documents successfully address the problems associated with rapid hair colour delivery. In particular, the problem of hair damage resulting from the use of high concentrations of hydrogen peroxide and ammonia to provide the required lift and colour and similarly the problem of scalp irritation again typically due to the presence of a high concentration of hydrogen peroxide and ammonia and also the high pH value are not satisfactorily resolved with current technologies and marketed products.

Another critical problem with the rapid colour compositions of the prior art is the delivery of the required resultant colour and also the effective coverage of grey hair; the amount and distribution of which varies considerably from consumer to consumer. The prior art not only does not deliver the required shade and depth of colour, but, in particular, also fails to meet the needs of consumers wishing to lighten their hair colour by a number of levels of lift. The delivery of such lightening requires significant bleaching which is currently only provided by compositions comprising high levels of hydrogen peroxide and which are utilised over an extended period of time on the hair in order to provide the consumer with the desired colour outcome. Likewise, the prior art compositions also do not deliver uniform and even colour on the hair or maintain the initial colour coverage achieved during the post dyeing washing and drying cycle.

Hence, it would be further desirable to provide the consumer with a hair colourant, providing desired levels of lift and lightening, as well as improved colour delivery and reduced damage, reduced skin and scalp irritation and low odour which is effective over shorter time periods of application than currently available products and which can be used as part of the consumer's regular beauty care routine. Moreover, it would also be desirable to provide a rapid colour delivery system whereby the difficulty in applying the composition onto the hair in a quick but thorough manner is addressed.

It has now been surprisingly found that oxidative hair colouring compositions comprising an oxidising agent, a source of carbonate ions and an alkalising agent utilised at pH 9.5 and below provide a rapidly acting hair bleach or colourant that delivers the required colour requiring less than 20 minutes development time on the hair of the consumer, whilst still delivering the required colour as currently utilised ammonia/peroxide systems requiring 45 minutes waiting time. Moreover, the method of the present invention reduces damage to the hair, reduces skin and scalp irritation, has low odour and is compatible with current dye and dye precursor systems, resulting in improved lift and lightening for blonde shades, excellent dye deposition, uniformity and colour, particularly grey coverage, which is maintained over consumers wash and styling cycle until the next colouring treatment. The method also allows for quick actual application of the compositions to the hair and minimises staining of the consumers skin, particularly along the hair line, whilst delivering the desired colour.

SUMMARY OF THE INVENTION

The present invention relates to a method of oxidative hair colouring and hair bleaching comprising the steps of providing a composition comprising i) at least one source of peroxymonocarbonate ions and ii) at least one source of alkalizing agent, preferably ammonium ions wherein said composition has a pH of up to and including 9.5 and then applying said composition to the hair and retaining said composition on the hair for a time period of less than 20 minutes and subsequently rinsing said composition from the hair.

In a further aspect the present invention relates to the use of a composition comprising i) at least one source of peroxymonocarbonate ions and ii) at least one source of alkalizing agent, preferably ammonium ions wherein said composition has a pH of up to and including 9.5 to oxidatively colour or bleach hair in less than 20 minutes.

Another aspect of the present invention relates to a method of sequential oxidative hair colouring or hair bleaching comprising the steps of at least two sequential oxidative hair colour or hair bleaching treatments wherein the time period between each treatment is from 1 day to 60 days, and wherein each treatment comprises the steps of providing a composition comprising i) at least one source of peroxymonocarbonate ions and ii) at least one source of alkalizing agent, preferably ammonium ions wherein said composition has a pH of less than 9.5 and then applying said composition to the hair and retaining said composition on the hair for a time period of less than 20 minutes and subsequently rinsing said composition from the hair.

Another aspect of the present invention relates to a method of pre-treatment of the hair whereby the hair is first applied with a pre-treatment composition comprising at least one conditioning agent which is retained on the hair prior to the application of the hair colouring or bleaching composition.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise.

Currently marketed hair permanent colourant products typically utilize a combination of an alkaliser system, dye precursors and an oxidant to deliver the desired hair colour to the consumer. The alkaliser is typically ammonia or an alkanolamine, such as monoethanolamine and the oxidant is typically hydrogen peroxide or a solid form of hydrogen peroxide. The final hair colour which is delivered to the consumer is a combination of the result of the underlying bleaching of the melanin pigment in the hair fibre and the delivery of the coloured dye chromophore moieties which are either preformed, that is direct dyes or are formed by oxidatization of the dye precursors within the hair fibre.

The optimal pH for such systems is typically about pH 10.0. This high pH is necessary in order to produce a sufficient concentration of the perhydroxy anion (HOO—) to give the desired bleaching of the melanin. It has been found that below pH 9.5 the concentration of this species is less than 0.01% of the added hydrogen peroxide concentration (pKa=11.6) and the amount of melanin bleaching drops dramatically and is hence insufficient to give the desired final colour.

However, as discussed herein above, compositions having a high pH cause many of the disadvantages noted by consumers for these colourant systems. In particular, the level of the volatile ammonia increases at high pH (above pH 9.5) giving increased unpleasant odour. Also, some consumers suffer from skin and scalp irritation. Furthermore, reactive species including the perhydroxy anions react with the hair fibre resulting in significant fibre damage. One consequence of this reactivity is that the hydrophilicity of the hair fibres is significantly increased and this causes an increase in the force required to comb the hair compared with hair that has not been coloured. Moreover, the higher forces that are exerted during combing and styling further result in increased fibre damage to the hair fibres.

It has now been surprisingly found that a method of colouring and bleaching hair whereby a composition comprising the combination of at least one source of peroxymonocarbonate ions, preferably formed insitu from a source of hydrogen peroxide and a carbonate ion source and at least one source of alkalizing agents, and preferably at least one source of radical scavenger, (as defined hereinafter), and preferably dyes and/or dye precursors, at a pH of up to and including 9.5, preferably 7.5 to 9.5, is applied to the hair of the consumer for a time period of less than 20 minutes can deliver improvements to the desired hair colour results, whilst considerably reducing the odour, skin and scalp irritation and damage to the hair fibres.

Whilst not wishing to be bound by theory, it is believed that in the present invention the key species responsible for the bleaching of the melanin, namely the peroxymonocarbonate ion (—OC(O)OOH), decomposes at pH values above 9.5 to form oxygen and the hydrogen carbonate ion. At pH values below 7.5 the hydrogen carbonate ion decomposes to form carbon dioxide and water. At pH values of 9.0 the bleaching of the melanin and the final colour observed is at an optimal level. Thus surprisingly the present invention allows for the delivery of improved lift, in other words hair lightening which is a highly desirable consumer need. Furthermore, compositions having a pH lower than 9.5 have the benefit that not only the unpleasant ammonia odour is significantly reduced but also the hair fibre damage is reduced. Moreover, due to the kinetics of the carbonate system the compositions require only a short development time on the hair of the consumers head of up to about 20 minutes in order to deliver improved uniform colour which is retained during the wash and styling cycle.

The compositions according to the present invention thus comprise a source of peroxymonocarbonate ions. These ions are typically formed insitu from the reaction between a source of hydrogen peroxide and carbonate ion. Consequently, the compositions according to the present invention comprise or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides and or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions), persulphates and combinations thereof.

According to the present invention the compositions comprise from about 0.1% to about 10% by weight, preferably from about 1% to about 7% by weight, and most preferably from about 2% to about 5% by weight of an oxidizing agent.

Carbonate Ion Source

According to the present invention the compositions thus also comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate and mixtures thereof.

The compositions of the present invention may comprise from about 0.1% to about 15%, preferably from about 0.1% to about 10% by weight, more preferably from about 1% to about 8% by weight of the carbonate ion. Preferably, if present, the ammonium ions and carbonate ions are present in the composition at a weight ratio of from 3:1 to 1:10, preferably 2:1 to 1:5. In a particularly preferred embodiment of the present invention the ammonium ions and carbonate ion sources are provided by a single source such as ammonium carbonate, ammonium hydrogen carbonate, ammonium hydrocarbonate or mixtures thereof.

Source of Alkalizing Agent

According to the present invention the composition also comprises at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof The compositions of the present invention may comprise from about 0.1% to about 10% by weight, preferably from about 0.5% to about 6%, most preferably from about 1% to about 3% of an alkalizing agent, preferably ammonium ions.

pH

According to the method of the present invention the compositions of the present invention have a pH up to and including pH 9.5. Preferably, the compositions of the present invention have a pH of from about 9.5 to about 7.5, more preferably from about 9.5 to about 8.4 and most preferably from about 9.4 to about 8.5 and even more preferably about pH 9.0.

Preferably the compositions of the present invention are prepared such that prior to application to the hair fibres the pH of the composition is no greater than about pH 9.5. However, in another embodiment of the present invention the compositions may be formulated such that the pH is up to 9.5 during the time period of application of the composition to the hair fibres prior to removal therefrom. Preferably, the pH is up to about 9.5 for at least 50% of the time period, preferably at least 70%, more preferably at least 80%, most preferably at least 90% of the time period of application of the composition to the hair.

The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

It is known that for good lightening and good colour formation that the final formulation should have a good buffering capacity or reserve alkalinity (the ability of the system to resist the pH shift that would otherwise be caused by addition of acid). The reserve alkalinity is measured using a Mettler DL70 auto-titrator with 0.1N methanolic hydrochloric acid being added to 0.7 mL of thoroughly mixed colourant product in 50 mL of methanol. The electrode is calibrated and then used to measure the amount of acid required to reach the sharpest end point triggered by a rapid change in pH. Using this method it has been determined that a reserve alkalinity of at least 0.2 ml of 0.1N of ethanolic hydrochloric acid and preferably above 0.4 is required for good lightening and colouring. Suitable buffering systems include ammonia/ammonium acetate mixtures, monoethanolamine tetrasodium pyrophosphate, isopropanolamine, benzoic acid Additional Components The compositions of the present invention may further comprise additional ingredients which include, but are not limited to, hair dyeing agents such as oxidative dye precursors, non-oxidative dyes, thickeners, solvents, enzymes, surfactants, conditioning agents, carriers, antioxidants, stabilizers, chelants, perming actives, perfume, reducing agents (thiolactic acid), hair swelling agents, hydrophobic oils such as coconut oil, mineral oil, isopropyl myristate, linseed oil and octyl palmitate and/or polymers. Some of these additional components are detailed hereafter.

Hair Dyes

The hair colouring compositions of the present invention are preferably hair colouring compositions which comprise oxidative dyeing compositions. Such compositions comprise oxidative hair dye precursors (also known as primary intermediates) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color.

The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are:

p-phenylenediamine derivatives, e.g. benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diaminophenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-2-methoxymethyl-phenol, 5-amino-2-hydroxy-benzoic acid, 1-(5-amino-2-hydroxyphenyl)-ethane-1,2-diol, 4-amino-2-(2-hydroxy-ethyl)-phenol, 4-amino-3-(hydroxymethyl)phenol, 4-amino-3-fluorophenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol; o-phenylenediamine derivatives such as: 3,4-Diaminobenzoic acid and salts thereof; o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxyphenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, pyrazolo[1,5-a]-pyrimidine-3,7-diamine, 5,6,7-trimethylpyrazolo[1,5-a]pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate.

Additional developers include N-(3-furylmethyl)benzene-1,4-diamine; N-Thiophen-3-ylmethyl-benzene-1,4-diamine;

N-(2-furylmethyl)benzene-1,4-diamine; N-Thiophen-2-yl-methyl-benzene-1,4-diamine; 4-Hydroxy-benzoic acid (2,5-diamino-benzylidene)-hydrazide; 3-(2,5-Diamino-phenyl)-N-ethyl-acrylamide; 2-[3-(3-Amino-phenylamino)-propenyl]-benzene-1,4-diamine; 2-[3-(4-Amino-phenylamino)-propenyl]-benzene-1,4-diamine; 2-(6-Methyl-pyridin-2-yl)-benzene-1,4-diamine; 2-Pyridin-2-yl-benzene-1,4-diamine; 2-[3-(4-Amino-phenylamino)-propenyl]-benzene-1,4-diamine; 2-[3-(3-Amino-phenylamino)-propenyl]-benzene-1,4-diamine; 3-(2,5-Diamino-phenyl)-N-ethyl-acrylamide; 2-Thiazol-2-yl-benzene-1,4-diamine; 4-Hydroxy-benzoic acid (2,5-diamino-benzylidene)-hydrazide; 3'-Fluoro-biphenyl-2,5-diamine; 2-Propenyl-benzene-1,4-diamine; 2'-Chloro-biphenyl-2,5-diamine; N-Thiophen-3-ylmethyl-benzene-1,4-diamine; N-(3-furylmethyl)benzene-1,4-diamine; 4'-Methoxy-biphenyl-2,5-diamine; N-(4-Amino-benzyl)-benzene-1,4-diamine; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; Biphenyl-2,4,4'-triamine hydrochloride; 5-(4-Amino-phenyl)aminomethyl-benzene-1,3-diamine hydrochloride; 5-Phenylaminomethyl-benzene-1,3-diamine hydrochloride; 2-[4-Amino-2-(3,5-diamino-benzylamino)-phenoxy]-ethanol hydrochloride; 5-(3-Amino-phenyl)aminomethyl-benzene-1,3-diamine hydrochloride; N-(2-Amino-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; 4-Amino-2-propylaminomethyl-phenol; hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide; hydrochloride; 4-Amino-2-(isopropylamino-methyl)-phenol; hydrochloride; 4-Thiophen-3-yl-benzene-1,3-diamine; hydrochloride hydrochloride; 5-Phenylaminomethyl-benzene-1,3-diamine hydrochloride; 5-(3-Amino-phenyl)aminomethyl-benzene-1,3-diamine hydrochloride; 4-Thiophen-3-yl-benzene-1,3-diamine; hydrochloride; 2',4'-Diamino-biphenyl-4-ol; hydrochloride; 5-Cyclobutylamino-2-methyl-phenol; 5-Cyclobutylamino-2-methyl-phenol; 4-Amino-2-(pyridin-3-ylaminomethyl)-phenol; 5-(3-Amino-phenyl)aminomethyl-benzene-1,3-diamine hydrochloride; 5-Allylaminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(4-Methoxy-benzyl)-benzene-1,3-diamine hydrochloride; N-Thiophen-2-ylmethyl-benzene-1,3-diamine hydrochloride; 4-Amino-2-[(2-hydroxy-5-nitro-phenylamino)-methyl]-phenol; hydrochloride; 2',4'-Diamino-biphenyl-4-ol hydrochloride; Biphenyl-2,4,4'-triamine; 5-(4-Amino-phenyl)aminomethyl-benzene-1,3-diamine hydrochloride; 2-[4-Amino-2-(3,5-diamino-benzylamino)-phenoxy]-ethanol hydrochloride; 5-Allylaminomethyl-benzene-1,3-diamine hydrochloride; 5-(3-Amino-phenyl)aminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(2-Amino-benzyl)-benzene-1,3-diamine hydrochloride; N-(4-Methoxy-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; N-Thiophen-2-ylmethyl-benzene-1,3-diamine hydrochloride; N-Benzo[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide hydrochloride; 4-Amino-2-propylaminomethyl-phenol; hydrochloride; 4-Amino-2-(isopropylamino-methyl)-phenol hydrochloride; 4-Amino-2-[(2-hydroxy-5-nitro-phenylamino)-methyl]-phenol hydrochloride; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; 5-Cyclobutylamino-2-methyl-phenol; 4-Amino-2-(pyridin-3-ylaminomethyl)-phenol; and 5-Cyclobutylamino-2-methyl-phenol.

Preferred developers include: p-phenylenediamine derivatives such as: 2-methyl-benzene-1,4-diamine; benzene-1,4-diamine; 1-(2,5-diamino-phenyl)-ethanol; 2-(2,5-diamino-phenyl)-ethanol; N-(2-methoxyethyl)benzene-1,4-diamine; 2-[(4-amino-phenyl)-(2-hydroxy-ethyl)-amino]-ethanol; 1-(2,5-diaminophenyl)ethane-1,2-diol; 1-(2'-Hydroxyethyl)-2,5-diaminobenzene; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylinediamine; and mixtures thereof; p-aminophenol derivatives such as: 4-amino-phenol, 4-methylamino-phenol, 4-amino-3-methyl-phenol, 4-amino-2-methoxymethyl-phenol; 1-(5-amino-2-hydroxy-phenyl)-ethane-1,2-diol; 1-Hydroxy-2,4-diaminobenzene; 1-(2'-Hydroxyethyloxy)-2,4-diaminobenzene; 4-Amino-2-aminomethylphenol; 2,4-Diamino-5-methylphenetol; 4-Amino-1-hydroxy-2-(2'-hydroxyethylaminomethyl)benzene; 1-methoxy-2-amino-4-(2'hydroxyethylamino)-benzene; 5-aminosalicylic acid and salts thereof; and mixtures thereof; o-phenylenediamine derivatives such as: 3,4-Diaminobenzoic acid and salts thereof; o-aminophenol derivatives such as: 2-amino-phenol, 2-amino-5-methyl-phenol, 2-amino-6-methyl-phenol, N-(4-amino-3-hydroxy-phenyl)-acetamide; 2-amino-4-methyl-phenol; and mixtures thereof; and heterocyclic derivatives such as: pyrimidine-2,4,5,6-tetramine; 1-methyl-1H-pyrazole-4,5-diamine; 2-(4,5-diamino-1H-pyrazol-1-yl)ethanol; 1-(4-methylbenzyl)-1H-pyrazole-4,5-diamine; 1-(benzyl)-1H-pyrazole-4,5-diamine; $N^2,N^2$-dimethyl-pyridine-2,5-diamine; 4-Hydroxy-2,5,6-triaminopyrimidine; 1-(2'hydroxyethyl)-amino-3,4-methylene dioxybenzene; and 1-Hydroxyethyl-4,5-diaminopyrazole sulphate; and mixtures thereof.

More preferred developers include: 2-methyl-benzene-1,4-diamine; benzene-1,4-diamine; N,N-Bis(2-hydroxyethyl)-p-phenylenediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol; and mixtures thereof.

Suitable couplers for use in the compositions described herein include, but are not limited to: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene; m-phenylenediamines such as: 2,4-diaminophenol, benzene-1,3-diamine, 2-(2,4-diaminophenoxy)-ethanol, 2-[(3-amino-phenyl)-(2-hydroxy-ethyl)-amino]-ethanol, 2-methyl-benzene-1,3-diamine, 2-[[2-(2,4- diamino-phenoxy)-ethyl]-(2-hydroxy-ethyl)-amino]-ethanol, 4-{3-[(2,4-diaminophenyl)oxy]-propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diaminophenyl)oxy]methoxy}-benzene-1,3-diamine, 1-methyl-2,6-bis(2-hydroxyethylamino)benzene; and 2,4-dimethoxybenzene-1,3-diamine; m-aminophenols such as: 3-aminophenol, 2-(3-hydroxy-4-methyl-phenylamino)-acetamide, 2-(3-hydroxy-phenylamino)-acetamide, 5-amino-2-methylphenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxy-propyl)amino]-2-methylphenol, 3-[(3-hydroxy-2-methylphenyl)-amino]propane-1,2-diol, 3-[(2-hydroxyethyl)amino]-2-methylphenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxyethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

Preferred couplers include: phenol, resorcinol, and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol; 1,2,4-Trihydroxybenzene; 1-Acetoxy-2-methylnaphthalene; and mixtures thereof; m-phenylenediamine derivatives such as: benzene-1,3-diamine, 2-(2,4-diamino-phenoxy)-ethanol, 4-{3-[(2,4-diaminophenyl)oxy]-propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol; 2,4-Diamino-5-(2'-hydroxyethyloxy)toluene; N,N-Dimethyl-3-ureidoaniline; 2,4-Diamino-5-fluorotoluenesulfatehydrate; 1-methyl-2,6-bis(2-hydroxyethylamino)benzene; and mixtures thereof; m-aminophenol derivatives such as: 3-amino-phenol, 5-amino-2-methyl-phenol, 5-(2-hydroxy-ethylamino)-2-methyl-phenol, and 3-amino-2-methyl-phenol; 1-Methyl-2-hydroxy-4-(2'-hydroxyethyl)aminobenzene; 1-Hydroxy-3-amino-2,4-dichlorobenzene; 1,3-Bis-(2,4-Diaminophenoxy)propane; 1-Hydroxy-2-methyl-5-amino-6-chlorobenzene; 5-Amino-4-chloro-2-methylphenol; and mixtures thereof; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, 2-aminopyridin-3-ol, 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole; 2,6-dihydroxypyridine; 2,6-dihydroxy-3,4-dimethylpyridine; 6-Hydroxybenzomorpholine; 2,6-Dihydroxy-3,4-dimethylpyridine; 3,5-Diamino-2,6-dimethoxypyridine; 3-Amino-2-methylamino-6-methoxypyridine; 1-Phenyl-3-methyl-5-pyrazolone-2,4-dihydro-5,2-phenyl-3H-pyrazole-3-one; and mixtures thereof.

More preferred couplers include: benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

Particularly preferred dyes for use herein include p-phenylene diamine, p-aminophenol, o-aminophenol, 2,5-diaminotoluene sulphate, p-methylaminophenol, N,N-bis-hydroxyethyl-p-phenylene diamine sulphate, 4-amino-2,6-dichlorophenol, m-aminophenol, 4-amino-20 hydroxytoluene, resorcinol, methylresorcinol, napthol, 2-amino-3-hydroxy pyridine, 2-amino-4-hydroxyethylamino anisole sulphate, 2-methyl-5-hydroxyethylaminophenol, m-phenylenediamine sulphate, 1-phenyl-3-methyl-5-pyrazolone, 1-hydroxyethyl-4,5-diamino pyrazole sulphate, 1-acetoxy-2-methylnapthalene and mixtures thereof.

The hair colouring compositions of the present invention may include non oxidative hair dyes i.e. direct dyes which may be used alone or in combination with the above described oxidative dyes. Suitable direct dyes include azo or anthraquinone dyes and nitro derivatives of the benzene series and or melanin precursors and mixtures thereof. Such direct dyes are particularly useful to deliver shade modification or highlights. In fact any molecule having the ability to impart a colour to the hair can be used. Of particluar importance in this respect are molecules containing either one or more of the following moieties: indigoids, polymethines, phthalocyanines, and aryl carboniums. These and other materials capable of imparting colour, as described in "Chromic Phenomena" by P. Bamfield (ISBN 0-85404-474-4, incorporated by reference) can all find application in the present invention. Of these materials, the preferred dyes are those disclosed in US2004/0078906 and of particular preference are the cationic azo dyes.

The hair dye compositions of the present invention will generally comprise from about 0.001% to about 10% of dyes. For example compositions providing low intensity dyeing such as natural blond to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Radical Scavenger

According to the present invention the compositions may further comprise a source of radical scavenger. As used herein the term radical scavenger refers to a species that can react with a carbonate radical to convert the carbonate radical by a series of fast reactions to a less reactive species, i.e. a carbonate radical scavenger.

Whilst not being bound by theory, it is believed that the ability of the radical scavenger to convert the carbonate radical (as described hereinabove) is dependant upon the energy of the charge transfer reaction as shown below: (The calculation of the energy of the charge transfer reaction is detailed hereinafter.)

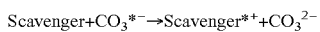

wherein the energy of the reaction is defined by:—

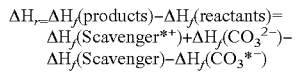

According to the present invention radical scavengers suitable for use herein have an energy of reaction of from about 0 kcal/mol to 14 kcal/mol, preferably from about 1.5 kcal/mol to 9 kcal/mol.

Suitable radical scavengers for use herein include compounds according to the general formula:

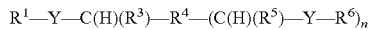

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H.

In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, N=$NA^1$, N=$NOA^1$, $NA^1CN$, $NA^1NA^2A^3$; (e) the group of monovalent substituents consisting of $COOA^1$, $CON_3$, $CONA^1{}_2$, $CONA^1COA^2$, C(=$NA^1$)$NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, 5$^{th}$ ed. (2001) at pages 368-375). Without being limited by theory, it is believed that substituents having sigma para values in the chosen ranges, when substituted onto $R^1$ and/or $R^2$, may improve the compound's toxicological profile without unduly adding an unfavourable increase in molecular weight that may interfere with the molecule's ability to penetrate the hair shaft. Some preferred substituents and their Hammett Sigma Para values are shown below, in Table A. Additional substituents and their values are shown in March, at page 370.

TABLE A

| Substituent | $NH_2$ | OH | H | COO— | Cl | COOH | $CF_3$ |
|---|---|---|---|---|---|---|---|
| $\sigma_p$ | −0.57 | −0.38 | 0 | 0.11 | 0.24 | 0.44 | 0.53 |

Preferably the above defined radical scavengers have a pKa of more than 7 to prevent the protonation of the nitrogen.

Alternative suitable radical scavengers for use herein are compounds according to the general formula (II):

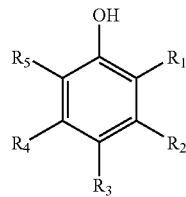
(II)

wherein $R_1$, $R_2$, $R_3$, $R_4$, and $R_5$ are each independently selected from H, $COO^-M^+$, Cl, Br, $So_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy group.

Other suitable radical scavengers for use herein include those selected from group (III) benzylamine, imidazole, di-tert-butylhydroxytoluene, hydroquinone, guanine, pyrazine, piperidine, morpholine, methylmorpholine, 2 methyoxyethylamine, and mixtures thereof.

Preferred radical scavengers according to the present invention are selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methyl-propan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof.

Especially preferred compounds are glycine, sarcosine, lysine, serine, 2 methoxyethylamine, glucosamine, glutamic acid, morpholine, piperdine, ethylamine, 3 amino-1-propanol and mixtures thereof.

The radical scavengers according to the present invention preferably have a molecular weight of less than about 500, preferably less than about 300, more preferably less than about 250 in order to facilitate penetration of the radical scavenger into the hair fibre. The compositions of the present invention preferably comprise from about 0.1% to about 10% by weight, preferably from about 1% to about 7% by weight of radical scavenger. Preferably, the radical scavenger is present at an amount such that the weight ratio of radical scavenger to carbonate ion is from 2:1 to 1:4. The radical scavenger is also preferably selected such that it is not an identical species as the alkalizing agent. According to one embodiment of the present invention the radical scavenger may be formed insitu in the hair dyeing compositions prior to application to the hair fibres.

Thickeners

The composition of the present invention may optionally further comprise at least about 0.01% of thickeners. Thickeners are preferably comprised in amount sufficient to provide the composition with a viscosity of from about 1 Pa·s to 40 Pa·s (1,000 to 40,000 cP) at 26° C. in order to provide a composition that can be readily applied to the hair without dripping. Suitable thickeners for use herein may be chosen, for example, from:
(i) associative thickeners;
(ii) crosslinked acrylic acid homopolymers;
(iii) crosslinked copolymers of (meth)acrylic acid and of (C1-C6)alkyl acrylate;
(iv) nonionic homopolymers and copolymers containing ethylenically unsaturated monomers of ester and amide type;
(v) ammonium acrylate homopolymers and copolymers of ammonium acrylate and of acrylamide;
(vi) polysaccharides; and
(vii) C12-C30 fatty alcohols.
(i) As used herein, the expression "associative thickener" means an amphiphilic thickener comprising both hydrophilic units and hydrophobic units, for example, at least one C8-C30 fatty chain and at least one hydrophilic unit. Representative associative thickeners that may be used are associative polymers chosen from:
(i) nonionic amphiphilic polymers comprising at least one fatty chain and at least one hydrophilic unit;
(ii) anionic amphiphilic polymers comprising at least one hydrophilic unit and at least one fatty-chain unit;
(iii) cationic amphiphilic polymers comprising at least one hydrophilic unit and at least one fatty-chain unit; and
(iv) amphoteric amphiphilic polymers comprising at least one hydrophilic unit and at least one fatty-chain unit;

The nonionic amphiphilic polymers comprising at least one fatty chain and at least one hydrophilic unit may, for example, be chosen from:
(1) celluloses modified with groups comprising at least one fatty chain; for example: hydroxyethylcelluloses modified with groups comprising at least one fatty chain chosen from alkyl, arylalkyl and alkylaryl groups, and in which the alkyl groups are, for example, C8-C22, such as the product Natrosol Plus Grade 330 CS(C16 alkyls) sold by the company Aqualon, and the product Bermocoll EHM 100 sold by the company Berol Nobel, and celluloses modified with polyalkylene glycol alkylphenyl ether groups, such as the product Amercell Polymer HM-1500 (polyethylene glycol (15) nonylphenyl ether) sold by the company Amerchol.
(2) hydroxypropyl guars modified with groups comprising at least one fatty chain, such as the product Esaflor HM 22 (C22 alkyl chain) sold by the company Lamberti, and the products Miracare XC95-3 (C14 alkyl chain) and RE205-1 (C20 alkyl chain) sold by the company Rhodia Chimie.
(3) polyether urethanes comprising at least one fatty chain, such as C10-C30 alkyl or alkenyl groups, for instance the products Elfacos T 210 and Elfacos T 212 sold by the company Akzo or the products Aculyn 44 and Aculyn 46 sold by the company Rohm & Haas.

(4) copolymers of vinylpyrrolidone and of fatty-chain hydrophobic monomers; examples that may be mentioned include: the products Antaron V216 and Ganex V216 (vinylpyrrolidone/hexadecene copolymer) sold by the company I.S.P., the products Antaron V220 and Ganex V220 (vinylpyrrolidone/eicosene copolymer) sold by the company I.S.P.

(5) copolymers of C1-C6 alkyl acrylates or methacrylates and of amphiphilic monomers comprising at least one fatty chain, such as the oxyethylenated methyl methacrylate/stearyl acrylate copolymer sold by the company Goldschmidt under the name Antil 208.

(6) copolymers of hydrophilic acrylates or methacrylates and of hydrophobic monomers comprising at least one fatty chain, such as polyethylene glycol methacrylate/lauryl methacrylate copolymer.

The anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, chosen from units derived from acrylic acids, methacrylic acids and mixtures thereof, wherein the fatty-chain allyl ether unit corresponds to the monomer of formula below:

CH2=C(R1)CH2OBnR    (I)

in which R1 is chosen from H and CH3, B is an ethyleneoxy radical, n is chosen from zero and integers ranging from 1 to 100, R is chosen from hydrocarbon-based radicals chosen from alkyl, arylalkyl, aryl, alkylaryl and cycloalkyl radicals, comprising from 10 to 30 carbon atoms, and, further, for example, from 10 to 24 carbon atoms and even further, for example, from 12 to 18 carbon atoms.

In one embodiment, a unit of formula (I) is, for example, a unit in which R1 can be H, n can be equal to 10 and R can be a stearyl (C18) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for example, diallyl phthalate, allyl (meth)acrylate, divinylbenzene, (poly)ethylene glycol dimethacrylate and methylenebisacrylamide.

Examples of such polymers are crosslinked terpolymers of methacrylic acid, of ethyl acrylate and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate and of steareth-10 allyl ether (40/50/10).

The anionic amphiphilic polymers may further be chosen, for example, from those comprising at least one hydrophilic unit of unsaturated olefinic carboxylic acid type, and at least one hydrophobic unit of the type such as a (C10-C30) alkyl ester of an unsaturated carboxylic acid. The hydrophilic unit of unsaturated olefinic carboxylic acid type corresponds to, for example, the monomer of formula (II) below:

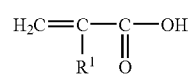

(II)

in which R1 is chosen from H, CH3, and C2H5, i.e. acrylic acid, methacrylic acid and ethacrylic acid units. And the hydrophobic unit of the type such as a (C10-C30) alkyl ester of an unsaturated carboxylic acid corresponds to, for example, the monomer of formula (III) below:

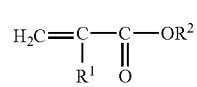

(III)

in which R1 is chosen from H, CH3, and C2H5 (i.e. acrylate, methacrylate and ethacrylate units) and is, for example, chosen from, for example, H (acrylate units) and CH3 (methacrylate units), R2 is chosen from C10-C30 alkyl radicals, for example, C12-C22 alkyl radical.

Examples of (C10-C30)alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are disclosed and prepared, for example, according to U.S. Pat. No. 3,915,921 and U.S. Pat. No. 4,509,949.

Representative anionic amphiphilic polymers that can be used may further be chosen from polymers formed from a mixture of monomers comprising:
(i) acrylic acid, an ester of formula (IV) below:

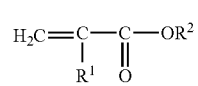

(IV)

in which R1 is chosen from H and CH3, R2 is chosen from C10-C30 alkyl radicals, such as alkyl radicals comprising from 12 to 22 carbon atoms, and a crosslinking agent; such as polymers derived from 95% to 60% by weight of the acrylic acid (hydrophilic unit), 4% to 40% by weight of C10-C30 alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of C10-C30 alkyl acrylate (hydrophobic unit) and 0.1% to 0.6% by weight of crosslinking polymerizable monomer; or
(ii) acrylic acid and lauryl methacrylate, such as the polymers formed from 66% by weight of acrylic acid and 34% by weight of lauryl methacrylate.

The crosslinking agent can be a monomer comprising a group (V)

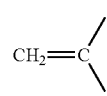

(V)

with at least one other polymerizable group whose unsaturated bonds are not conjugated with respect to one another. Mention may be made, for example, of polyallyl ethers such as polyallylsucrose and polyallyl pentaerythritol.

Among said polymers above mention may be made, for example, of the products sold by the company Noveon under the trade names Pemulen TR1, Pemulen TR2, Carbopol 1382, and further, for example, Pemulen TR1, and the product sold by the company S.E.P.C. under the name Coatex S X.

Suitable anionic amphiphilic fatty-chain polymers, include for example the methacrylic acid/methyl acrylate/ethoxylated alkyl dimethyl-meta-isopropenylbenzylisocyanate copolymer sold under the name Viscophobe DB 1000 by the company Amerchol.

The cationic amphiphilic polymers used are, for example, chosen from quaternized cellulose derivatives and polyacrylates comprising amino side groups.

The quaternized cellulose derivatives are, for example, chosen from; quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof.

Quaternized and non-quaternized polyacrylates comprising amino side groups having for example, hydrophobic groups, such as Steareth 20 (polyoxy-ethylenated(20) stearyl alcohol) and (C10-C30)alkyl PEG-20 itaconate.

The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Examples of quaternized alkylhydroxyethyl-celluloses comprising C8-C30 fatty chains are the products Quatrisoft LM 200, Quatrisoft LM-X 529-18-A, Quatrisoft LM-X 529-18B (C12 alkyl) and Quatrisoft LM-X 529-8 (C18 alkyl) sold by the company Amerchol, and the products Crodacel QM, Crodacel QL (C12 alkyl) and Crodacel QS (C18 alkyl) sold by the company Croda.

Examples of polyacrylates comprising amino side chains is Structure Plus from the company National Starch.

Among amphoteric amphiphilic polymers comprising at least one hydrophilic unit and at least one fatty-chain unit, mention may be made, for example, of methacrylamidopropyltrimethylammonium chloride/acrylic acid/C10-C30 alkyl methacrylate copolymers, wherein the alkyl radical is, for example, a stearyl radical.

(ii) Among the crosslinked acrylic acid homopolymers that may be mentioned are those crosslinked with an allylic alcohol ether of the sugar series, such as the products sold under the names Carbopol 980, 981, 954, 2984 and 5984 by the company Noveon or the products sold under the names Synthalen M, Synthalen L and Synthalen K by the company 3V Sigma.

(iii) Crosslinked copolymers of (meth)acrylic acid and of C1-C6 alkyl acrylate can be chosen from crosslinked copolymers of methacrylic acid and of ethyl acrylate as an aqueous dispersion comprising 38% active material sold, for example, under the name Viscoatex 538C by the company Coatex, and crosslinked copolymers of acrylic acid: and of ethyl acrylate as an aqueous dispersion comprising 28% active material sold under the name Aculyn 33 by the company Rohm & Haas. Crosslinked copolymers of methacrylic acid and of ethyl acrylate include an aqueous dispersion comprising 30% active material manufactured and sold under the name Carbopol Aqua SF-1 by the company Noveon.

(iv) Among the nonionic homopolymers or copolymers comprising ethylenically unsaturated monomers of ester and/or amide type, mention may be made of the products sold under the names: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); BPA 500 by the company Kobo (polymethyl methacrylate).

(v) Ammonium acrylate homopolymers that may be mentioned include the product sold under the name Microsap PAS 5193 by the company Hoechst.

Copolymers of ammonium acrylate and of acrylamide include the product sold under the name Bozepol C Nouveau or the product PAS 5193 sold by the company Hoechst (which are described and prepared in documents FR-2 416 723, U.S. Pat. No. 2,798,053 and U.S. Pat. No. 2,923,692).

(vi) The polysaccharides are, for example, chosen from glucans, modified and unmodified starches (such as those derived, for example, from cereals, for instance wheat, corn or rice, from vegetables, for instance yellow pea, and tubers, for instance potato or cassaya), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, succinoglucans, gum arabics, gum tragacanths, ghatti gums, karaya gums, carob gums, galactomannans, such as guar gums, and nonionic derivatives thereof (hydroxypropyl guar) and xanthan gums, and mixtures thereof.

For example, suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., the content of these three publications being entirely incorporated by reference.

For example, starches, guar gums and celluloses and derivatives thereof can be used. Suitable starches include for example, of macromolecules in the form of polymers comprising elemental moieties that are anhydroglucose units. The number of these moieties and their assembly make it possible to distinguish between amylose (linear polymer) and amylopectin (branched polymer). The relative proportions of amylose and of amylopectin, and also their degree of polymerization, can vary as a function of the botanical origin of the starches. The botanical origin of the starch molecules used may be cereals or tubers. Thus, the starches can be, for example, chosen from corn starch, rice starch, cassaya starch, tapioca starch, barley starch, potato starch, wheat starch, sorghum starch and pea starch. Starches are generally in the form of a white powder, which is insoluble in cold water and which has an elementary particle size ranging from 3 to 100 microns. The starches may optionally be C1-C6 hydroxyalkylated or C1-C6 acylated (such as acetylated). The starches may also have undergone heat treatments. Distarch phosphates or of compounds rich in distarch phosphate, for instance the products sold under the references Prejel VA-70-T AGGL (gelatinized hydroxypropylated cassaya distarch phosphate) or Prejel TK1 (gelatinized cassaya distarch phosphate) or Prejel 200 (gelatinized acetylated cassaya distarch phosphate) by the company Avebe, or Structure ZEA from National Starch (hydroxypropylated corn distarch phosphate), Structure XL from National Starch (hydroxypropylated starch phosphate) may also be used.

The guar gums may be modified or unmodified. The unmodified guar gums are, for example, the products sold under the name Vidogum GH 175 by the company Unipectine and under the names Meyro-Guar 50 and Jaguar C by the company Meyhall. The modified nonionic guar gums are, for example, modified with C1-C6 hydroxyalkyl groups. Among hydroxyalkyl groups, mention may be made, for example, of hydroxymethyl, hydroxyethyl, hydroxypropyl and hydroxybutyl groups. These guar gums are well known in the state of the art and can be prepared, for example, by reacting corresponding alkene oxides, such aspropylene oxides, with guar gum so as to obtain a guar gum modified with hydroxypropyl groups. The degree of hydroxyalkylation, which corresponds to the number of alkylene oxide molecules consumed by the number of free hydroxyl functions present on the guar gum, may, for example, range from 0.4 to 1.2.

Such nonionic guar gums optionally modified with hydroxyalkyl groups are sold, for example, under the trade names Jaguar HP8, Jaguar HP60 and Jaguar HP120, Jaguar DC 293 and Jaguar HP 105 by the company Rhodia Chimie (Meyhall) or under the name Galactasol 4H4FD2 by the company Aqualon.

Suitable celluloses include for example, hydroxyethylcellulose and hydroxypropylcelluloses, such as the products sold under the names Klucel EF, Klucel H, Klucel LHF, Klucel MF and Klucel G by the company Aqualon.

(vii) The C12- C30 fatty alcohols are, for example, chosen from myristyl alcohol, cetyl alcohol, stearyl alcohol, behenyl alcohol or mixture thereof. When fatty alcohols are used as thickeners, at least one additional surfactant with HLB value above about 6 is commonly included to form bi-layers with fatty alcohols. The most useful bi-layer structures include gel network phase where parallel bi-layers of fatty alcohols are swollen by water forming semi-solid creams, and vesicle dispersions where fatty alcohols bi-layers are curved into approximately spherical uni-lamellar or multi-lamellar aggregates.

Preferred for use herein are salt tolerant thickeners. A non exclusive list of suitable salt tolerant thickeners for use herein include xanthan, guar, hydroxypropyl guar, scleroglucan, methyl cellulose, ethyl cellulose (commercially available as Aquacote®), hydroxyethyl cellulose (Natrosol®), carboxymethyl cellulose, hydroxypropylmethyl cellulose, microcrystalline cellulose, hydroxybutylmethyl cellulose, hydroxypropyl cellulose (Klucel®), hydroxyethyl ethyl cellulose, cetyl hydroxyethyl cellulose (Natrosol® Plus 330), N-vinylpyrollidone (Povidone®), Acrylates/Ceteth-20 Itaconate Copolymer (Structure® 3001), hydroxypropyl starch phosphate (Structure® ZEA), polyethoxylated urethanes or polycarbamyl polyglycol ester (e.g. PEG-150/Decyl/SMDI copolymer=Aculyn® 44, PEG-150/Stearyl/SMDI copolymer=Aculyn 46®), trihydroxystearin (Thixcin®) acrylates copolymer (e.g. Aculyn® 33) or hydrophobically modified acrylate copolymers (e.g. Acrylates/Steareth-20 Methacrylate Copolymer=Aculyn® 22), and Crodafos CES®.

Conditioning Agent

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Particularly useful conditioning materials are cationic polymers. Conditioners of cationic polymer type may be chosen from those already know by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituant that is directly attached to the main polymer chain. Such cationic polymers generally have a number average molecular mass ranging from 500 to $5 \times 10^6$, or more preferably from 1000 to $3 \times 10^6$. Polymers of the polyamine, polyamino amide and polyquaternary ammonium type that may be used include but are not limited to:

1) Homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Examples of such polymers include:

Copolymers of acrylamide and of methacryloyloxyethyltrimethylammonium methosulfate, examples of which include polymers known via the INCI nomenclature as Polquaternium-5, such as the products sold under the names Reten 210, Reten 220, Reten 230, Reten 240, Reten 1104, Reten 1105, Reten 1006 by the company Hercules and Merquat 5, Merquat 5 SF by the company Nalco.

Copolymers of vinylpyrrolidone and dimethylaminopropyl methacrylamide, examples of which include polymers known via the INCI nomenclature as Polyquaternium-28, such as the products sold under the name Gafquat HS-100 by the company International Speciality Products (ISP).

Coplolymers of vinyl pyrrolidone and dialkyaminoalkyl acrylates or methactylates, examples of which include polymers known via the INCI nomenclature as Polquatemium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryldimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name Merquat 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name Hypan QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium-43, such as the products sold under the name Bozequat 4000 by the company Clairant.

Copolymers of acrylic acid, methylacrylate and methacrylamidopropyltrimonium chloride, examples of which include polymers known via the INCI nomenclature as Polyquatemium-47, such as the products sold under the name Merquat 2001 and Merquat 2001N sold commercially by Nalco.

Copolymes of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name Plascize L-450 by the company Goo Chemcial.

Copolymers of acrylic acid diallyl dimethyl ammonium chloride and acrylamide, examples of which include polymers known via the INCI nomenclature as polyquaternium 39, such as the products sold under the name Merquat 3330 and Merquat 3331 by the company Nalco.

Further examples include copolymers of methacrylamide methacrylamido-propyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name Rohagit KF 720 F by the company Rohm, Polyquaternium-30, such as the products sold under the name Mexomere PX by the company Chimex, Polyquaternium-33, Polyquaternium-35, Polyquaternium-36, such as the products sold under the name Plex 3074 L by the company Rhon, Polyquaternium 45, such as the products sold under the name Plex 3073L by the company Rohn, Polyquatemium 49, such as the products sold under the name Plascize L-440 by the company Goo Chemicals, Polyquaternium 50 such as the products sold under the name Plascize L-441 by the company Goo Chemicals, Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to Copolymers of hydroxyethylcelluloses and diallyldimethyl ammonium chlorides, examples of which include polymers known via the INCI nomenclature as Polyquaternium-4, such as the products sold under the name Celquat L 200 and Celquat H 100 by the company National Starch.

Copolymers of hydroxyethylcelluloses and a trimethyl ammonium substituted epoxide, examples of which include polymers known via the INCI nomenclature as Polyquaternium-10, such as the products sold under the name AEC Polyquatemium-10 by the company A&E Connock, Catinal C-100 Catinal HC-35 Catinal HC-100 Catinal HC-200 Catinal LC-100 Catinal LC-200 by the company Toho, Celquat SC-240C Celquat SC-230M, by the company National Starch, Dekaquat 400, Dekaquat 3000 by the company Dekker, Leogard GP by the company Akzo Nobel, RITA Polyquta 400 RITA, Polyquta 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name Quatrisoft polymer LM-200 by the company Amerchol.

Derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epxoypropyl/diethylenetriamine.

5) Cyclopolymers of dialkdiallylamine or of dialkyldiallyammonium, among which polymers mention may be made of:

Dimethyldiallyammonium chloride polymers, examples of which include polymers known via the INCI nomenclature as Polyquatemium-6, such as the products sold under the name Merquat 100 by the company Nalco, Mirapol 100 by the company Rhodia, Rheocare CC6 by the company Cosmetic Rheologies, AEC polyquaternium-6 by the company A&E Connock, Agequat 400 by the company CPS, Conditioner P6 by the company 3V Inc., Flocare C106 by the company SNF, Genamin PDAC by the company Clariant, Mackernium 006 by the company McIntyre.

Copolymers of acrylamides and dimethyldiallylammonium chlorides monomers, examples of which include polymers known via the INCI nomenclature as Polyquaternium-7, such as the products sold under the name AEC Polyquaternium-7 by the company A&E Connock, Agequat-5008, Agequat C-505 by the company CPS, Conditioner P7 by the company 3V Inc. Flocare C 107 by the company SNF Mackemium 007, Mackernium 007S by the company McIntyre, ME Polymer 09W by the company Toho, Merquat 550, Merquat 2200, Merquat S by the company Nalco, Mirapol 550 by the company Rhodia, Rheocare CC7, Rheocare CCP7 by the company Cosmetic Rheologies, Salcare HSP-7, Salcare SC10, Salcare Super 7 by the company Ciba.

Copolymers of dimethyldiallylammoniumchlorides and acrylic acids, examples of which include polymers known via the INCI nomenclature as polyquatemary-22, such as the products sold under the name Merquat 280 and Merquat 295 by the company Nalco.

6) Quaternary diammonium polymers comprising repeat units corresponding to [—N+(R1)(R2)-A1-N+(R3)(R4)-B1-][2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are choen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An examples of which include polymers known via the INCI nomenclature as Hexadimethrine chloride, where R1, R2, R3 and R4 are each methyl radicals, A1 is (CH2)3 and B1 is (CH2)6 and X=Cl. Further examples of which include polymers known via the INCI nomenclature as polyquatemium-34 where R1 and R2 are ethyl radicals and R3 and R4 are methyl radicals and A1 is (CH2)3 and B1 is (CH2)3 and X=Br, such as the products sold under the name Mexomere PAX by the company Chimax.

7) Polyquaternary ammonium polymers comprising repeating units of formula [—N+(R6)(R7)-(CH2)r—NH—CO—(CH2)q—CO)t—NH—(CH2)s—N+(R8)(R9)-A-] [2X—], in which R6, R7, R8 and R9 which may be identical or different, are chosen from a hydrogen atom and a methyl, ethyl, propyl, α-hydroxyethyl, α-hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2-CH2-O—CH2-CH2-. Examples of which include Polymers known via the INCI nomenclature as polyquatemium-2, where r=s=3, q=0,t=0, R6, R7, R8 and R9 are methyl groups, and A is —CH2-CH2-O—CH2-CH2, such as the products sold under the name Ethpol PQ-2 from Ethox and Mirapol A-15 by the company Rhodia.

Polymers known via the INCI nomenclature as polyquaternium-17 where r=s=3, q=4, t=1 R6, R7, R8 and R9 are methyl groups, and A is —CH2-CH2-O—CH2-CH2.

Polymers known via the INCI nomenclature as Polyquatemium 18, where r=s=3, q=7, t=1 R6, R7, R8 and R9 are methyl groups, and A is —CH2-CH2-O—CH2-CH2

Polymers known via the INCI nomenclature as the block copolymer formed by the reaction of Polyquaternium-2 with Polyquaternium-17, known as Polyquaternium 27, such as the products sold under the name Mirapol 175 by the company Rhodia.

8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name Luviquat FC370, Luviquat FC550, Luviquat FC905, Luviquat HM-552 by the company BASF. Or copolymers of vinylcaprolactams and vinylpyrrolidones with rnethylvinylimidazolium methosulfates, examples of which include polymers known via the INCI nomenclature as Polyquaternium-46, such as the products sold under the name Luviquat Hold by the company BASF. Or copolymers of vinylpyrrolidones and quaternized imidazolines, examples of which include polymers known via the INCI nomenclature poylquaterary 44, such as the products sold under the name Luviquat Care by the company BASF 9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4) alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name Synthalen, C N Synthalen C R, Synthalen C U, sold by 3V sigma, or as a dispersion in another media such as the products sold under the name Salcare SC95 and Salcare SC96 by the company Ciba or Rheocare CTH(E) by the company Cosmetic Rheologies. Or in another example of which include polymers known via the INCI nomenclature as Polyquatemium-32, or when sold as a dispersion in mineral oil such as the products sold under the name Salcare SC92 by the company Ciba.

11) Further examples of cationic polymers include polymers known via the INCI nomenclature as Polyquatemium 51, such as the products sold under the name Lipidure-PMB by the company NOF, via the INCI nomenclature as Polyquaternium 54, such as the products sold under the name Qualty-Hy by the company Mitsui, and via the INCI nomenclature as Polyquaternium 56 such as the products sold under the name Hairrol UC-4 by the company Sanyo chemicals.

12) Silicone polymers comprising cationic groups and/or groups which may be ionised into cationic groups. For example: cationic silicones of the general formula (R10-N+(CH3)2)-R11(Si(CH3)2-O)x-R11-(N+(CH3)2)-R10), where R10 is an alkyl derived from coconut oil, and R11 is (CH2CHOCH2O(CH2)3 and x is a number between 20 and 2000, examples of which include polymers known by the INCI nomenclature as Quaternium 80, such as the products sold under the name as Abil Quat 3272 and Abil Quat 3474 sold commercially by Goldschmidt.

Silicones containing groups which may be ionised into cationic groups, for example aminosilicones containing at least 10 repeating siloxane —(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R12O)(CH3)2Si—O where R12 can be either OH or OR13, where R13 is a C1-C8 alky group, or a mixture of both functional terminal groups, known by the INCI nomenclature as amodimethicone, such as the products sold under the name as Wacker Belsil ADM 1100, Wacker Belsil ADM 1600, Wacker Belsil ADM 652, Wacker Belsil ADM 6057E, Wacker Belsil ADM 8020 sold commercial by Wacker Silicones, DC929, DC939, DC949 and DC AP6087 sold commercially by Dow Corning and SM2059 sold commercially by GE silicones.

Silicones containing groups which may be ionised into cationic groups—for example silicones containing at least 10 repeating siloxane —(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know by the INCI nomenclature as methoxy PEG/PPG-7/3 Aminopropyl Dimethicone, such as the product sold under the name of Abil Soft AF100 sold commercially by Degussa. For example products know by the INCI nomenclature as Bis (C13-15 Alkoxy) PG Amodimethicone, such as the product sold under the name of DC 8500 sold commercially by Dow Corning.

Surfactants

The compositions according to the present invention may further comprise one or more surfactants. Surfactants suitable for use herein generally have a lipophilic chain length of from about 8 to about 30 carbon atoms and can be selected from anionic, nonionic, amphoteric and cationic surfactants and mixtures thereof. The total level of surfactant is from about 1% to about 60%, preferably from about 2% to about 30%, more preferably from about 8% to about 25% and especially from about 10% to about 20% by weight.

The compositions of the invention preferably comprise a mixture of anionic and amphoteric surfactants with one or more nonionic surfactants. Anionic components, where may be present in the range of from about 0.1% to about 20%, preferably from about 0.1% to about 15%, and more preferably from about 5% to about 15% by weight of the composition; amphoteric or nonionic components, may independently be present is in the range from about 0.1% to about 15% by weight, preferably from about 0.5% to about 10%, more preferably from about 1% to about 8% by weight.

As examples of anionic surfactants, which can be used, alone or as mixtures, mention may be made, for example, of salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates and N-acyltaurates. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated ($C_6$-$C_{24}$) alkyl ether carboxylic acids, polyoxyalkylenated ($C_6$-$C_{24}$) alkylaryl ether carboxylic acids, polyoxyalkylenated ($C_6$-$C_{24}$) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used.

The nonionic surfactants are compounds that are well known (see, for example, in this respect "Handbook of Surfactants" by M. R. Porter, published by Blackie & Son (Glasgow and London), 1991, pp. 116-178). They can be chosen, for example, from polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

The amphoteric surfactants can be chosen, for example, from aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$)alkylsulphobetaines. Among the amine derivatives, mention may be made of the products sold under the name Miranol, as described, for example, in U.S. Pat. Nos. 2,528,378 and 2,781,354 and having the structures of:

$$R_2\text{—CON HCH}_2\text{CH}_2\text{—N}^+(R_3)(R_4)(\text{CH}_2\text{COO}^-) \quad (VI)$$

in which: $R_2$ is chosen from alkyl radicals derived from an acid $R_2$—COOH present in hydrolysed coconut oil, and heptyl, nonyl and undecyl radicals, $R_3$ is a β-hydroxyethyl group and $R_4$ is a carboxymethyl group; and of $$R_5\text{—CONHCH}_2\text{CH}_2\text{—N(B)(C)} \quad (VII)$$

wherein B represents —$CH_2CH_2OX'$, C represents —$(CH_2)_z$—Y', with z=1 or 2, X' is chosen from the —$CH_2CH_2$—COOH group and a hydrogen atom, Y' is chosen from —COOH and —$CH_2$—CHOH—$SO_3H$ radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid. Salts of diethyl aminopropyl cocoaspartamid can be also used.

The cationic surfactants may be chosen from: A) the quaternary ammonium salts of general formula (VIII) below:

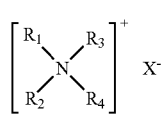
(VIII)

wherein $X^-$ is an anion chosen from halides (chloride, bromide and iodide), $(C_2-C_6)$alkyl sulphates, such as methyl sulphate, phosphates, alkyl and alkylaryl sulphonates, and anions derived from organic acids, such as acetate and lactate, and i) the radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy and alkylamide radicals, $R_4$ is chosen from linear and branched alkyl radicals comprising from 16 to 30 carbon atoms.

The cationic surfactant is, for example, a behenyltrimethylammonium salt (for example chloride).

ii) the radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals can comprise at least one hetero atom such as oxygen, nitrogen, sulphur and halogens. The aliphatic radicals are chosen, for example, from alkyl, alkoxy, alkylamide and hydroxyalkyl radicals comprising from about 1 to 4 carbon atoms;

$R_3$ and $R_4$ which may be identical or different, are chosen from linear and branched alkyl radicals comprising from 12 to 30 carbon atoms, the said alkyl radicals comprise at least one function chosen from ester and amide functions.

$R_3$ and $R_4$ are chosen, for example, from $(C_{12}-C_{22})$alkylamido$(C_2-C_6)$alkyl and $(C_{12}-C_{22})$alkylacetate radicals.

The cationic surfactant is, for example, a dicetyldimethyl ammonium salt (for example chloride);

B)-the quaternary ammonium salts of imidazolinium, such as that of formula (IX) below:

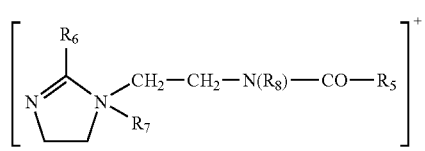
(IX)

in which $R_5$ is chosen from alkenyl and alkyl radicals comprising from 8 to 30 carbon atoms, for example fatty acid derivatives of tallow, $R_6$ is chosen from a hydrogen atom, $C_1-C_4$ alkyl radicals and alkenyl and alkyl radicals comprising from 8 to 30 carbon atoms, $R_7$ is chosen from $C_1-C_4$ alkyl radicals, $R_8$ is chosen from a hydrogen atom and $C_1-C_4$ alkyl radicals, and $X^-$ is an anion chosen from halides, phosphates, acetates, lactates, alkyl sulphates, alkyl sulphonates and alkylaryl sulphonates.

In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), which are sold under the names "Rewoquat®" W75, W90, W75PG and W75HPG by the company Witco, C)-the diquaternary ammonium salts of formula (X):

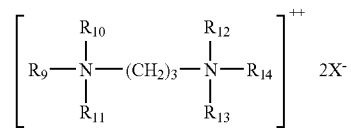
(X)

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride; and D)-the quaternary ammonium salts comprising at least one ester function, of formula (XI) below:

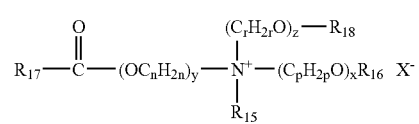
(XI)

in which:

R15 is chosen from C1-C6 alkyl radicals and C1-C6 hydroxyalkyl and dihydroxyalkyl radicals; R16 is chosen from: a radical R19C(O)—, linear and branched, saturated and unsaturated C1-C22 hydrocarbon-based radicals R20, and a hydrogen atom, R18 is chosen from: a radical R21C (O)—, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X-is an anion chosen from simple and complex, organic and inorganic anions; with the proviso that the sum x+y+z is from 1 to 15, that when x is 0, then R16 is R20 and that when z is 0, then R18 is R22.

In one embodiment, the ammonium salts of formula (XV) can be used, in which: R15 is chosen from methyl and ethyl radicals, x and y are equal to 1; z is equal to 0 or 1; n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21 C(O)— and a hydrogen atom. Such compounds are sold, for example, under the names Dehyquart by the company Cognis, Stepanquat by the company Stepan, Noxamium by the company Ceca, and Rewoquat WE 18 by the company Rewo-Witco.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation issues may arise.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol.

Finally, the compositions according to the present invention can be provided in any usual form, such as for example an aqueous composition, a powder, a gel or an oil-in-water emulsion. A preferred form for the compositions according to the present invention are thickened solutions comprising a salt-tolerant thickener or oil-in-water emulsions.

Pre-treatment Compositions

According to one aspect of the method of the present invention the hair is treated with a pre-treatment composition prior to application of the hair colourant or bleaching compositions. Pre-treatment compositions according to the present invention comprise at least one conditioning agent. As used herein, the term "conditioning agent" refers to any agent whose function is to improve at least one cosmetic property of keratin materials such as hair, for example the softness, smoothness, disentangling, feel and static electricity. The at least one conditioning agent may be soluble or insoluble in water.

Any of the conditioning agents listed herein above as conditioning agents and surfactants may be suitable for use in the pre-treatment composition. Particularly preferable are cationic polymers, silicone materials, anionic polymers, non-ionic polymers, oils and waxes, emulsions made from lamellar liquid crystals and mixtures thereof.

Emulsions made from lamellar liquid crystals which are formed by the combination of several actives provide improvement in the cosmetic properties of the composition such as conditioning properties. This arises due to the presence of a combination of fatty materials and an emulsifier to from an emulsion. Emulsifiers for use in the aqueous continuous phase of the emulsion may include an anionic surfactant, cationic surfactant, amphoteric surfactant, water-soluble polymeric surfactant, water-soluble silicone-containing surfactant, non-ionic surfactant having an HLB of greater than about 10, or a surfactant system capable of forming stabilizing liquid crystals. The nonionic surfactant preferably has an HLB of at least 12, and more preferably, an HLB value of at least about 15. Surfactants belonging to these classes are listed in McCutcheon's Emulsifiers and Detergents, North American and International Editions, MC Publishing Co., Glen Rock N.J., pages 235-246 (1993).

The emulsifier for the aqueous phase does not gel the aqueous phase. The emulsifier however may be capable of forming a stabilizing layer of lamellar liquid crystals. For conciseness, the term "liquid crystal structure" as used herein, should be taken to also include gel networks, which are solidified liquid crystals. The surfactant system can be a single surfactant or a blend of surfactants. In some cases, a particular surfactant cannot form a liquid crystal structure alone, but can participate in the formation of liquid crystals in the presence of a second surfactant.

Exemplary classes of surfactants capable of participating in the formation of a liquid crystal, include but are not limited to specific cationic surfactants, anionic surfactants, nonionic surfactants, quaternary ammonium surfactants and lipid surfactants.

Preferred non-ionic surfactants for the formation of liquid crystals in the aqueous continuous phase are of the nonionic type and include C16-20 fatty alcohols, and C16-20 fatty alcohol ethoxylates with 1 to 30 ethylene oxide groups. Specific examples include cetearyl alcohol, cetyl alcohol, stearyl alcohol, arachidyl alcohol, oleyl alcohol, ceteareth ethoxylates with between 10 and 30 ethylene oxide groups, ceteth ethoxylates with between 10 to 30 ethylene oxide groups, steareth ethoxylates with between 10 and 30 ethoxylates, and combinations thereof. Preferably, C16-22 fatty alcohols are used in combination with C16-22 fatty alcohol ethoxylates at a ratio of between 10:1 to 0.5:1, more preferably between 6:1 and 1:1, and most preferably between 5:1 and 1.5:1.

Preferred cationic surfactants contain quaternary ammonium compounds of formula: [R18R19R20R21N]+X—, where R18 is an alkyl or alkenyl group having from about 8 to 22 carbon atoms, R19 and R20 are both independently either an alkyl or alkenyl group having from about 8 to 22 carbon atoms or alkyl or hydroxyalkyl group having from about 1 to 4 carbon atoms, R21 is an alkyl or hydroxyalkyl group having from about 1 to 4 carbon atoms, and X— is a salt forming anion (e.g. chloride, bromide, acetate, alkylsulfate).

Advantageously, in order to facilitate formation of liquid crystals, the surfactant system may also comprise amidoamines of the following general formula: R22CONH(CH2)m N (R23)2, wherein R22 is a residue of C8 to C24 fatty acids, R23 is a C1 to C4 alkyl, and m is an integer from 1 to 4. Preferred amidoamine useful in the present invention includes stearamidopropyldimethylamine, stearamidopropyldiethylamine, stearamidoethyl-diethylamine, stearamidoethyldimethylamine, palmitamidopropyl-dimethylamine, palmitamido-propyldiethylamine, palmitamidoethyl-diethylamine, palmitamido-ethyldimethylamine, behenamidopropyldimethylamine, behenamido-propyldiethylamine, behenamidoethyl-diethylamine, behenamidoethyldimethylamine, arachidamidopropyldimethylamine, arachidamido-propyidiethylamine, arachidamidoethyl-diethylamine, arachidamidoethyl-dimethylamine, and mixtures thereof; more preferably stearamido-propyidimethylamine, stearamidoethyidiethylamine, and mixtures thereof.

More advantageously, the amidoamines are partially quaternized with acids selected from the group consisting of L-glutamic acid, lactic acid, hydrochloric acid, malic acid, succinic acid, acetic acid, fumaric acid, L-glutamicio acid hydrochloride, tartaric acid, and mixtures thereof; preferably L-glutamic acid, lactic acid, hydrochloric acid, and mixtures thereof. Preferably, the mole ratio of amidoamine to acid is from about 1:0.3 to about 1:1, more preferably from about 1:0.5 to about 1:0.

Polymers suitable as conditioning agents include anionic and nonionic polymers which may be water-soluble or water insoluble. Suitable anionic polymers include polymers comprising at least one group derived from carboxylic acid, sulphonic acid or phosphoric acid and such as those having a weight-average molecular weight ranging from 500 to 5,000,000, determined, for example, by gel permeation chromatography.

Suitable nonionic polymers include for example, from the following polymers:—vinylpyrrolidone homopolymers; copolymers of vinylpyrrolidone and vinyl acetate; polyalkyloxazolines such as the polyethyloxazolines sold by the company Dow Chemical under the names "Peox 50 000", "Peox 200 000" and "Peox 500 000"; vinyl acetate homopolymers, such as the product sold under the name "Appretan EM" by the company Hoechst, and the product sold under the name "Rhodopas A 012" by the company Rhodia Chimie; copolymers of vinyl acetate and acrylic ester, such as the product sold under the name "Rhodopas AD 310" by Rhodia Chimie; copolymers of vinyl acetate and ethylene, such as the product sold under the name "Appretan TV" by the company Hoechst; copolymers of vinyl acetate and maleic ester, for example of dibutyl maleate, such as the product sold under the name "Appretan MB Extra" by the company Hoechst; copolymers of polyethylene and maleic anhydride; alkyl acrylate homopolymers and alkyl methacrylate homopolymers, such as the product sold under the name "Micropearl RQ 750" by the company Matsumoto or the product sold under the name "Luhydran A 848 S" by the company BASF; acrylic ester copolymers such as copolymers of alkyl acrylates and alkyl methacrylates, such as the products sold by the company Rohm & Haas under the names "Primal AC-261 K" and "Eudragit NE 30 D", by the company BASF under the names "Acronal 601", "Luhydran LR 8833" and 8845, and by the company Hoechst under the names "Appretan N 9213" or N 9212; copolymers of acrylonitrile and a nonionic monomer chosen, for example, from butadiene and alkyl (meth)acrylates; mention may be made of the products sold under the names "Nipol LX 531 B" by the company Nippon Zeon and those sold under the name "CJ 0601 B" by the company Rohm & Haas; polyurethanes, such as the products sold under the names "Acrysol RM 1020" and "Acrysol RM 2020" by the company Rohm & Haas, and the products "Uraflex XP 401 UZ" and "Uraflex XP 402 UZ" by the company DSM Resins; copolymers of alkyl acrylate and urethane, such as the product "8538-33" by the company National Starch; polyamides, such as the product "Estapor LO 11" sold by the company Rhodia Chimie; and unmodified and chemically modified nonionic guar gums.

Examples of oils suitable for use as conditioning agents in the pre-treatment method of the present invention include both animal and plant oils, and are for example, chosen from sunflower oil, corn oil, soybean oil, avocado oil, jojoba oil, marrow oil, grapeseed oil, sesame oil, hazelnut oil, fish oils, glyceryl tricaprocaprylate, and plant and animal oils of formula $R_9COOR_{10}$ in which R9 is chosen from higher fatty acid residues containing from 7 to 29 carbon atoms and $R_{10}$ is chosen from linear and branched hydrocarbon-based chains containing from 3 to 30 carbon atoms, such as alkyl and alkenyl, for example, purcellin oil and liquid jojoba wax.

The waxes are natural (animal or plant) or synthetic substances that are solid at room temperature (20°-25° C.). They are insoluble in water, soluble in oils and are capable of forming a water-repellent film. The waxes are chosen, for example, from carnauba wax, candelilla wax, alfalfa wax, paraffin wax, ozokerite, plant waxes such as olive tree wax, rice wax, hydrogenated jojoba wax and absolute waxes of flowers such as the essential wax of blackcurrant flower sold by the company Bertin (France), animal waxes such as beeswaxes, and modified beeswaxes (cerabellina). Other waxes or waxy starting materials, which can be used, include, for example, marine waxes such as the product sold by the company Sophim under the reference M82, and polyethylene waxes and polyolefins in general.

The pre-treatment compositions preferably comprise a conditioning agentcomprising an emulsion made from lamellar liquid crystals, more preferably a fatty alcohol and surfactant emulsion. The pre-treatment composition has a viscosity of from 100 Pa to 300 Pa, preferably from 115 Pa to 285 Pa, more preferably from 130 Pa to 250 Pa, most preferably from 160 Pa to 240 Pa. The pre-treatment composition typically comprises from 0.2 to 20%, preferably from 1.0 to 15%, most preferably from 5 to 15% of said conditioning agents and preferably has a pH of from 3 to 7, more preferably from pH 4 and pH 6.

The pre-treatment composition may further comprise additional adjuncts, which are selected so as not to eliminate or substantially reduce the performance or shelf stability of the composition. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, pearlescents, opacifiers, enzymes, suspending agents, antimicrobials, preservatives, proteins, herb and plant extracts, bleach, peroxide, polyols, silicones, solvents, antibodies, pH adjusting agents including pH buffers, viscosity modifiers, preservatives, viscosity enhancers, gelling agents, chelators, oxidising agents, reducing agents, UV filters, emulsifying agents, antioxidants, moisturizing and conditioning agents, and other common adjuvants well known to those skilled in the art.

According to the present invention it has been surprisingly found that the application of the pre-treatment composition to the hair prior to the application of the hair colouring or bleaching composition, preferably, without prior rinsing provides a number of unexpected benefits. Firstly, the presence of the pre-treatment composition on the hair allows for easier application of the colouring or bleaching composition as the hair neither separates too quickly or on the contrary tangles upon application of the composition to the hair particularly along the length of the hair. Consequently the compositions can be applied both more quickly and more effectively. Secondly, the pre-treatment composition also prevents skin staining by the hair colourant compositions. Thirdly, the pre-treatment compositions deliver conditioning benefits which are consumer noticeable already at time of removal of the colourant or bleaching composition. Consequently the pre-treatment method reduces the need for a final conditioning step which thus speeds up the time required by the consumer to complete the process.

Oxidative hair dye compositions are usually sold in kits comprising, in individually packaged components such as separate containers, a dye component (also called "dye cream" for emulsions or "dye liquid" for solutions) comprising the oxidative dye, precursors and alkalizing agent which is typically ammonia in a suitable carrier and; a hydrogen peroxide component (also called "hydrogen peroxide cream" for emulsions or "hydrogen peroxide liquid" for solutions) comprising the oxidizing agent (usually hydrogen peroxide). The consumer mixes the dye component and hydrogen peroxide component together immediately before use and applies it onto the hair. The exemplified formulations given in the tables hereinafter illustrate these resulting mixtures.

Similarly, bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aesrosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to: the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

Method of Use

According to the present invention the method of colouring or bleaching hair comprises after applying the composition to the hair and preferably working the mixture for a few minutes (to insure uniform application to all of the hair), the composition is allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual. It can be observed that the hair will have as changed from its original color to the desired color.

According to an alternative embodiment of the present invention, the method of colouring and or bleaching the hair is a sequential oxidative hair colouring or hair bleaching method comprising the steps of at least two sequential oxidative hair colour or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes.

According to another embodiment of the present invention the method of colouring or bleaching comprises a pre-treatment step whereby a pre-treatment composition comprising at least one conditioning agent is applied to the hair and without subsequent rinsing, the hair colourant or bleaching composition is then applied. Such a pre-treatment composition would also typically be packaged in a separate container.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers.

For the compositions comprising a radical scavenger, the scavenger may be comprised within the dye component, the hydrogen peroxide component, the pre-treatment composition, if present, or may be comprised as a separate radical scavenger component, separately packaged. Similarly, for the bleaching composition, the radical scavenger may be comprised within the ammonium ion source component, the oxidising agent component, or the second oxidising agent component, the pre-treatment composition if present or within a separate radical scavenger component, or comprised within two or more of the components. Preferably, however the radical scavengers are comprised within the dye component. The radical scavenger is typically applied to the hair during or after any pre-treatment composition application but prior to the application of the hair colourant or bleaching composition. Alternatively the radical scavenger is mixed with the dye or oxidant component.

In another embodiment of the present invention the kit may comprise a separate component comprising other sensitive materials such as certain dyes for example dyes cationic azo dyes which are not stable in the main dye component.

The kits described hereinabove are well known in the art and the composition in each container can be manufactured utilizing any one of the standard approaches, these include a) 'Oil in water' process, b) 'Phase Inversion' process and c) 'One-pot' process.

For example, in a 'One-pot' process, the polymers and chelants would be pre-dissolved in water, the fatty materials added and then the whole composition heated to about 70-80° C. A controlled cooling and optional shearing process to form the final structured product in the case of an emulsion would then follow. Addition of the materials providing source of peroxymonocarbonate ions, radical scavengers and ammonia, and optionally solvents, dyes and pH trimming complete the making process of the dye cream.

In the case of a liquid solution comprising acrylate polymers, these would be formulated into the hydrogen peroxide component. The glycol solvents and fatty components are formulated into the dye component. A structured product is formed when the dye and hydrogen peroxide components are mixed together prior to use of the composition, resulting from deprotonation of the polymer acrylic acid groups as the pH rises, yielding a polymeric micro-gel. Further details on the manufacture of these two-part aqueous composition for coloring hair, which forms a gel on mixing of the two parts can be found in U.S. Pat. No. 5,376,146, Casperson et al. and U.S. Pat. No. 5,393,305, Cohen et al.

The composition of the present invention can also be formulated as 2-part aqueous compositions comprising polyetherpolyurethane as thickening agent (such as Aculyn ® 46) as described in U.S. Pat. Nos. 6,156,076 and 6,106,578.

EXAMPLES

The following examples illustrate oxidative dye compositions according to the present invention and methods of manufacture thereof.

Examples of Emulsion Formulations 1-10

| Ingredient | Formulation | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Ammonium Carbonate | 3.0 | 6.0 | 2.0 | — | 4.0 | 8.0 | 2.0 | — | 4.0 | 6.0 |

-continued

| Ingredient | \multicolumn{10}{c}{Formulation} |
|---|---|---|---|---|---|---|---|---|---|---|
|  | 1 | 2 | 3 | 4 | 5 | 6 | 7 | 8 | 9 | 10 |
| Potassium Hydrogen Carbonate | — | — | 1.5 | 2.0 | — | — | 2.0 | 2.0 | — | — |
| Ammonium Acetate | — | — | — | 2.0 | — | — | — | 2.0 | — | — |
| Ceteareth-25 | 1.0 | — | — | — | — | — | — | 1.0 | 1.0 | 1.0 |
| Steareth-100 | — | 1.0 | 1.0 | — | — | — | — | — | — | — |
| Sodium Palmytoyl Sarcosinate | — | — | — | — | 1.0 | — | — | — | — | — |
| Sodium Carboxymethyl Lauryl Glucoside | — | — | — | 1.0 | — | — | — | — | — | — |
| Sodium Lauryl Sulfate | — | — | — | — | — | 1.0 | — | — | — | — |
| Behentrimonium Chlorid | — | — | — | — | — | — | 1.0 | — | — | — |
| Cetyl Alcohol | 1.6 | — | 2 | 1.5 | 1.5 | 1.5 | 2.5 | 2.5 | 1.6 | 1.6 |
| Stearyl Alcohol | 3.3 | — | 2 | 1.5 | 1.5 | 1.5 | 2.5 | 2.5 | 3.3 | 3.3 |
| Steareth-2 | — | 5 | 1 | — | — | — | — | — | — | — |
| Sodium Benzoate | 0.1 | 0.1 | 0.1 | 0.1 | 0.1 | 0.1 | 0.1 | 0.1 | 0.1 | 0.1 |
| Phenoxyethanol | 0.1 | 0.1 | 0.1 | 0.1 | 0.1 | 0.1 | 0.1 | 0.1 | 0.1 | 0.1 |
| EDTA (tetrasodium salt) | 0.1 | 0.1 | 0.1 | 0.1 | 0.1 | 0.1 | 0.1 | 0.1 | 0.1 | 0.1 |
| Sodium Glycinate | 2.0 | 5.0 | 3.0 | 1.0 | — | — | — | — | — | 3.0 |
| Glutamic Acid | — | — | — | — | — | 6.0 | 2.0 | — | — | — |
| Glycine | — | — | — | 1.0 | 2.0 | — | — | — | — | — |
| Glucosamine | — | — | — | — | — | — | 2.0 | 4.0 | 4.0 | 3.0 |
| Para-phenylene-diamine | 0.8 | 0.5 | 0.6 | 0.5 | 0.8 | 0.8 | 0.5 | 0.6 | 0.5 | 0.8 |
| Para-aminophenol | 0.2 | 0.3 | 0.2 | 0.1 | 0.2 | 0.2 | 0.3 | 0.2 | 0.1 | 0.2 |
| Meta-aminophenol | 1.0 | 0.5 | 1.0 | 0.6 | 1.0 | 1.0 | 0.5 | 1.0 | 0.6 | 1.0 |
| Resorcinol | 1.6 | 1.2 | 1.6 | 0.8 | 1.6 | 1.6 | 1.2 | 1.6 | 0.8 | 1.6 |
| Hydrogen Peroxide (35% active) | 8.6 | 8.6 | 8.6 | 12.9 | 17 | 17 | 17 | 10.7 | 10.7 | 10.7 |
| Amodimethicone (Belsil ADM1100) | 1.5 | — | — | — | — | — | — | — | 1.0 | — |
| Trimethylsilylamo-dimethicone (SF1708) | — | 0.5 | — | — | — | — | — | 2.0 | — | — |
| Polyquaternium-22 (Merquat 295) | — | — | 2.0 | — | 0.1 | — | — | — | — | — |
| Polyquaternium-37 & Mineral oil (Salcare SC95) | — | — | — | 0.5 | 0.1 | — | — | — | — | — |
| Polyquaternium 10 (Polymer JR30M) | — | — | — | — | — | 0.2 | 0.2 | — | — | — |
| Dicetyldimonium Chloric | — | — | — | — | — | — | — | — | 0.2 | — |
| Xanthan gum | 0.1 | 0.5 | — | — | 0.2 | — | — | — | — | — |
| Cetyl hydroxyethyl Cellulose (Natrosol 330C Plus) | — | — | 0.8 | — | — | — | — | — | — | — |
| pH adjust to pH 9.0 | qs | qs | qs | qs | qs | qs | qs | qs | qs | qs |
| Water | qs | qs | qs | qs | qs | qs | qs | qs | qs | qs |

Examples of Emulsion Formulations 11-20

| Ingredient | \multicolumn{10}{c}{Formulation} |
|---|---|---|---|---|---|---|---|---|---|---|
|  | 11 | 12 | 13 | 14 | 15 | 16 | 17 | 18 | 19 | 20 |
| Sodium sulphite | 0.1 | 0.1 | 0.1 | 0.1 | 0.1 | 0.1 | 0.1 | 0.1 | 0.1 | 0.1 |
| Erythorbic Acid | 0.2 | 0.2 | 0.2 | 0.2 | 0.2 | 0.2 | 0.2 | 0.2 | 0.2 | 0.2 |
| Ammonium Carbonate | 3.0 | 6.0 | 2.0 | — | 4.0 | 8.0 | 2.0 | — | 4.0 | 6.0 |
| Potassium Hydrogen Carbonate | — | — | 1.5 | 2.0 | — | — | 2.0 | 2.0 | — | — |
| Ammonium Acetate | — | — | — | 2.0 | — | — | — | 2.0 | — | — |
| Crodafos ® CES | 2.0 | 3.0 | 4.0 | 3.0 | 3.0 | 3.0 | 3.0 | 3.0 | 3.0 | 3.0 |
| EDTA (tetrasodium salt) | 0.1 | 0.1 | 0.1 | 0.1 | 0.1 | 0.1 | 0.1 | 0.1 | 0.1 | 0.1 |
| EDDS (disodium salt) | — | — | — | — | — | 2.5 | — | — | — | — |
| Sodium Glycinate | 3.0 | 5.0 | 2.0 | 1.0 | — | — | — | — | — | 3.0 |
| Glutamic Acid | — | — | — | — | — | 6.0 | 2.0 | — | — | — |
| Glycine | — | — | — | 1.0 | 2.0 | — | — | — | — | — |
| Glucosamine | — | — | — | — | — | — | 2.0 | 4.0 | 4.0 | 3.0 |
| Dipropylene glycol | 5.0 | 1.0 | 5.0 | 4.0 | 5.0 | 5.0 | 3.0 | 4.0 | 3.0 | 5.0 |
| Para-phenylene-diamine | 0.8 | 0.006 | 0.6 | 0.5 | 0.8 | 0.8 | 0.5 | 0.6 | 0.5 | 0.8 |

-continued

| Ingredient | Formulation | | | | | | | | | |
|---|---|---|---|---|---|---|---|---|---|---|
| | 11 | 12 | 13 | 14 | 15 | 16 | 17 | 18 | 19 | 20 |
| Para-aminophenol | 0.2 | — | — | 0.1 | 0.2 | 0.2 | 0.3 | 0.2 | 0.1 | 0.2 |
| Meta-aminophenol | 1.0 | — | — | 0.6 | 1.0 | 1.0 | 0.5 | 1.0 | 0.6 | 1.0 |
| Resorcinol | 1.6 | 0.012 | 1.6 | 0.8 | 1.6 | 1.6 | 1.2 | 1.6 | 0.8 | 1.6 |
| 1-Naphthol | — | — | 0.2 | — | — | — | — | — | — | — |
| Hydrogen Peroxide (35% active) | 8.6 | 12.8 | 8.6 | 12.9 | 17 | 17 | 17 | 10.7 | 10.7 | 10.7 |
| Amodimethicone (Belsil ADM1100) | 1.5 | — | — | — | — | — | — | — | 1.0 | — |
| Trimethylsilylamo-dimethicone (SF1708) | — | — | — | — | — | — | — | 2.0 | — | — |
| Polyquaternium-22 (Merquat 295) | — | — | 2.0 | — | 0.5 | — | — | — | — | — |
| Polyquaternium-37 & Mineral oil (Salcare SC95) | — | — | — | 0.5 | 0.1 | — | — | — | — | — |
| Styrene-PVP copolymer (Antara 430) | 0.2 | 1.0 | 0.7 | 1.0 | 2.0 | 2.00 | 2.0 | 0.6 | 0.6 | 0.6 |
| Dicetyldimonium Chloric | — | — | — | — | — | — | — | — | 0.2 | — |
| Xanthan gum | 0.1 | — | — | 0.2 | — | — | — | — | — | — |
| Succinoglycan | — | — | — | — | 0.2 | 0.5 | — | — | — | — |
| Carbomer | — | — | — | — | — | — | 1.0 | 0.5 | — | — |
| Acrylates/C10-30 Alkyl Acrylate Crosspolymer | — | — | — | — | — | — | — | 0.5 | — | — |
| Hydroxyethyl cellulose | — | — | — | — | — | — | — | — | 0.5 | — |
| Hydroxypropyl Starch Phosphate | — | — | — | — | — | — | — | — | — | 2.0 |
| pH adjust to pH 9.0 | qs | qs | qs | qs | qs | qs | qs | qs | qs | qs |
| Water | qs | qs | qs | qs | qs | qs | qs | qs | qs | qs |

Examples of Thickened Aqueous Solution Formulations 1-10

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Citric Acid | 1.0 | 1.0 | 1.0 | 1.0 | 1.0 | 1.0 | 1.0 | 1.0 | 1.0 | 1.0 |
| Ammonium Carbonate | 3.0 | 6.0 | 2.0 | — | 4.0 | 8.0 | 2.0 | — | 4.0 | 6.0 |
| Potassium Hydrogen Carbonate | — | — | 1.5 | 2.0 | — | — | 2.0 | 2.0 | — | — |
| Ammonium Acetate | — | — | — | 2.0 | — | — | — | 2.0 | — | — |
| Oleth 10 | 1.0 | 1.0 | 1.0 | 1.0 | — | — | — | — | — | — |
| Oleth 2 | 0.8 | 0.8 | 0.8 | 0.8 | — | — | — | — | — | — |
| Oleic Acid | 0.9 | 0.9 | 0.9 | 0.9 | — | — | — | — | — | — |
| Cocamide DEA | 3.0 | 3.0 | 3.0 | 3.0 | — | — | — | — | — | — |
| EDTA (tetrasodium salt) | 0.1 | 0.1 | 0.1 | 0.1 | 0.1 | 0.1 | 0.1 | 0.1 | 0.1 | 0.1 |
| Sodium Glycinate | 2.0 | 5.0 | 3.0 | 1.0 | — | — | — | — | — | — |
| Glutaminc Acid | — | — | — | — | — | 6.0 | 2.0 | — | — | — |
| Glycine | — | — | — | 1.0 | 2.0 | — | — | — | — | — |
| Glucosamine | — | — | — | — | — | — | — | 2.0 | 4.0 | 4.0 | 3.0 |
| Para-phenylene Diamine | 0.8 | 0.5 | 0.6 | 0.5 | 0.8 | 0.8 | 0.5 | 0.6 | 0.5 | 0.8 |
| Para-aminophenol | 0.2 | 0.3 | 0.2 | 0.1 | 0.2 | 0.2 | 0.3 | 0.2 | 0.1 | 0.2 |
| Meta-aminophenol | 1.0 | 0.5 | 1.0 | 0.6 | 1.0 | 1.0 | 0.5 | 1.0 | 0.6 | 1.0 |
| Resorcinol | 1.6 | 1.2 | 1.6 | 0.8 | 1.6 | 1.6 | 1.2 | 1.6 | 0.8 | 1.6 |
| Hydrogen Peroxide (35% active) | 8.6 | 8.6 | 8.6 | 13 | 17 | 17 | 17 | 10.7 | 10.7 | 10.7 |
| Polyquaternium-22 (Merqu 295) | — | — | — | — | 0.5 | — | — | — | — | — |
| Polyquaternium-37 & Mine (Salcare SC95) | — | — | — | — | 0.1 | — | 0.5 | — | — | — |
| Amodimethicone (Belsil ADM1100) | — | — | — | — | — | 1.0 | — | — | — | — |
| Acrylates Copolymer (Aculyn ® 33A) | 2.4 | 2.4 | 2.4 | 2.4 | — | — | — | — | — | — |

-continued

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| Acrylates Steareth-20 Methacrylate Copolymer (Aculyn ® 22) | 0.5 | 0.5 | — | 1.0 | — | — | — | — | — | — |
| Xanthan gum | — | — | — | — | — | 1.0 | — | — | — | — |
| Succinoglycan | — | — | — | — | 0.8 | — | — | — | — | — |
| Carbomer | — | — | — | — | — | — | 2.0 | — | — | — |
| Acrylates/C10-30 Alkyl Acrylate Crosspolymer | — | — | — | — | — | — | — | 2.0 | — | — |
| Hydroxyethyl cellulose | — | — | — | — | — | — | — | — | 2.0 | — |
| Hydroxypropyl Starch Phosphate | — | — | — | — | — | — | — | — | — | 2.0 |
| Propylene Glycol | 8.2 | 8.2 | 8.2 | 8.2 | 8.0 | 8.0 | 8.0 | 8.0 | 8.0 | 8.0 |
| Ethoxy Diglycol | 4.2 | 4.2 | 4.2 | 4.2 | — | — | — | — | — | — |
| pH adjust to pH 9.0 | qs | qs | qs | qs | qs | qs | qs | qs | qs | qs |
| Water | qs | qs | qs | qs | qs | qs | qs | qs | qs | qs |

Pre-treatment Composition Examples

Pre-treatment compositions 1-6 below were made by heating the water to 80° C. then adding the glutamic acid and stearamidopropyl dimethylamine and fatty alcohols, EDTA and benzyl alcohol and mixing. The mixture is then cooled to below the phase transition, the additional ingredients added and then cooled to 30° C. The mixture is them milled using a Silverson SL2 for 3 minutes.

| Composition | 1 | 2 | 3 | 4 | 5 | 6 |
|---|---|---|---|---|---|---|
| Cetyl alcohol | 1.05 | 2.8 | 2.45 | 1.4 | 1.75 | 1.75 |
| Stearyl alcohol | 1.89 | 5.04 | 4.41 | 2.52 | 3.15 | 3.15 |
| Stearamidopropyl dimethyamine | 0.84 | 2.24 | 1.96 | 1.12 | 1.40 | 1.40 |
| L-Glutamic acid | 0.27 | 0.72 | 0.63 | 0.36 | 0.45 | 0.45 |
| Tetrasodium EDTA (87%) | 0.03 | 0.08 | 0.07 | 0.04 | 0.05 | 0.05 |
| Benzyl alcohol | 0.12 | 0.32 | 0.28 | 0.16 | 0.20 | 0.20 |
| Kathon CG | 0.009 | 0.024 | 0.021 | 0.012 | 0.015 | 0.015 |
| silicone | 1.50 | 4.00 | 3.50 | 2.00 | 2.50 | 2.50 |
| Demineralised water | qs | qs | qs | qs | qs | qs |
| Rheology 850 $s^{-1}$ | 115 | 355 | 280 | 175 | 225 | 225 |

An AR 500 rotational rheometer (TA Instruments Ltd., Leatherhead, Surrey KT22 7UQ, UK) is used to determine the viscosity of the pre-treatment compositions. The determination is performed at 26.7° C., with the 4 cm 2° steel cone measuring system set with a 50 μm (micron) gap and is performed via the programmed application of a shear rate from 0.5 to 1000 1/s over a 1 minute time period with 10 data points recorded per decade. These data are used to create a shear rate vs. shear stress curve for the material. The value obtained on the plotted graphs at 850 $s^{-1}$ is recorded.

The exemplified pre-treatment compositions described hereinabove may be applied to wet or dry (preferably dry) hair. Immediately prior to use, the dye component and the oxidant component are mixed together. The resultant mixture is then applied to the hair. If the consumer has not coloured their hair previously, or if they are changing their hair colour from the previous colour, the mixture is applied to the whole of the hair by massaging the product into the hair, starting at the roots and ending at the tips (a so called 'full head application'). Once the application is complete a further amount of time between 6-15 minutes (preferably 10 minutes) is allowed for the colour to develop. The product is then rinsed from the hair with warm water until no more dye will rinse out. A conditioner product can then optionally be applied.

If the consumer is colouring with the same colour (a so called 'root touch up application') then after the dye component and oxidant component are mixed, a portion of the mixture is applied first to the roots of the hair. Once application to the roots is complete, a period of 5-9 mins is allowed for the colour to develop. The remaining mixture is then applied to the rest of the hair and a further period (after application is complete) of between 1 and 10 minutes is allowed for the colour to develop. Preferably the total amount of time allowed for development is 10 minutes or less. After the development time is complete the product is rinsed from the hair as described in the full head application description hereinabove.

If a pretreatment composition is being used, this composition is applied first to the dry hair. The pretreatment composition remains on the hair without rinsing whilst the 'full head application' or 'root touch up application' protocols described above are used. In the instance where the pretreatment is an effective conditioner it may be possible for the consumer to omit the final separate conditioning treatment from the regime—this simplifies the procedure and makes it faster overall.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are the scope of this invention.

What is claimed is:

1. A method of oxidatively colouring or bleaching hair in less than about 20 minutes comprising the steps of:
   i) providing a composition comprising at least one source of peroxymonocarbonate ions and at least one source of alkalizing agent, wherein said composition has a pH of from about 7.5 to about 9.5 ii) applying said composition on the hair and maintaining said composition on the hair for a time period of less than about 20 minutes, and subsequently iii) rinsing said composition from the hair.

2. A method of sequential oxidative hair colouring or hair bleaching comprising the steps of at least two sequential oxidative hair colour or hair bleaching treatments wherein the time period between each treatment is from about 1 to about 60 days and wherein each treatment comprises the steps of i) providing a composition comprising at least one source of peroxymonocarbonate ions and at least one source of alkalizing agent, wherein said composition has a pH of from about 7.5 to about 9.5, and then ii) applying said composition to the hair and retaining said composition on the hair for a time period of less than about 20 minutes and subsequently iii) rinsing said composition from the hair.

3. A method of colouring or bleaching hair according to claim 1, wherein said method further comprises a first pre-treatment step, wherein a pre-treatment composition comprising at least one conditioning agent is applied to the hair.

4. A method of colouring or bleaching hair according to claim 3, wherein said pre-treatment composition is not rinsed from the hair prior to the next step.

5. A method of colouring or bleaching hair according to claim 1, wherein said composition is maintained on the hair for a time period of less than about 15 minutes.

6. A method of colouring or bleaching hair according to claim 1, wherein said source of peroxymonocarbonate ions comprises at least one source of hydrogen peroxide and at least one source of carbonate ions, carbamate ions, hydrocarbonate ions, or mixtures thereof.

7. A method of colouring or bleaching hair according to claim 1, wherein said at least one source of alkalizing agent is a source of ammonium ions.

8. A method of colouring or bleaching hair according to claim 6, wherein said composition comprises:
   b. from about 0.1% to about 10% by weight of said at least one source hydrogen peroxide;
   c. from about 0.1% to about 10% by weight of said at least one source of alkalizing agent; and
   d. from about 0.1% to about 15% by weight of said at least one source of carbonate ions, carbamate ions, hydrocarbonate ions, or mixtures thereof.

9. A method of colouring or bleaching hair according to claim 1, wherein said composition further comprises at least one oxidative dye and or at least one direct dye.

10. A method of colouring or bleaching hair according to claim 1, wherein said composition further comprises a radical scavenger.

11. A method of colouring or bleaching hair according to claim 1, wherein said composition further comprises a chelating agent.

* * * * *